(12) United States Patent
Bae et al.

(10) Patent No.: US 9,876,791 B2
(45) Date of Patent: Jan. 23, 2018

(54) METHOD AND APPARATUS FOR AUTHENTICATING USER BASED ON BIOSIGNAL

(71) Applicant: Samsung Electronics Co., Ltd., Suwon-si (KR)

(72) Inventors: Chisung Bae, Yongin-si (KR); HaiBing Ren, Suwon-si (KR); YongNan Ji, Suwon-si (KR); Xuetao Feng, Beijing (CN); Biao Wang, Suwon-si (KR); Sangjoon Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 93 days.

(21) Appl. No.: 14/983,112

(22) Filed: Dec. 29, 2015

(65) Prior Publication Data

US 2016/0191517 A1    Jun. 30, 2016

(30) Foreign Application Priority Data

Dec. 30, 2014    (KR) .................. 10-2014-0194107

(51) Int. Cl.
*H04L 29/06*    (2006.01)
*A61B 5/00*    (2006.01)
(Continued)

(52) U.S. Cl.
CPC ........ *H04L 63/0861* (2013.01); *A61B 5/0452* (2013.01); *A61B 5/117* (2013.01); *A61B 5/7246* (2013.01)

(58) Field of Classification Search
CPC ... H04L 63/0861; G06F 21/32; A61B 5/0452; A61B 5/117; A61B 5/7246
(Continued)

(56) References Cited

U.S. PATENT DOCUMENTS 7,617,058 B2    11/2009    Kim et al.
7,689,833 B2    3/2010    Lange
(Continued)

FOREIGN PATENT DOCUMENTS

KR    10-0750662 B1    8/2007
KR    10-0946766 B1    3/2010
(Continued)

OTHER PUBLICATIONS

Extended European Search Report dated May 31, 2016 in counterpart European Application No. EP 15187290.0 (7 pages).

*Primary Examiner* — Syed Zaidi
(74) *Attorney, Agent, or Firm* — NSIP Law

(57) ABSTRACT

A method and apparatus for authenticating a user are provided. An authentication apparatus includes a data set generator configured to generate an authentication data set by extracting waveforms from a biosignal of a user, a similarity calculator configured to match each of the extracted waveforms to registered waveforms included in a registration data set, and calculate a similarity between each of the extracted waveforms and the registered waveforms, and an auxiliary similarity calculator configured to extract a representative authentication waveform indicating a representative waveform of the extracted waveforms and a representative registration waveform indicating a representative waveform of the registered waveforms, and calculate a similarity between the representative authentication waveform and the representative registration waveform.

24 Claims, 11 Drawing Sheets

(51) Int. Cl.
*A61B 5/0452* (2006.01)
*A61B 5/117* (2016.01)

(58) Field of Classification Search
USPC .............................................................. 726/7
See application file for complete search history.

(56) References Cited

U.S. PATENT DOCUMENTS

| | | |
|---|---|---|
| 8,200,319 B2 | 6/2012 | Pu et al. |
| 8,489,181 B1 | 7/2013 | Schipper et al. |
| 2004/0249294 A1 | 12/2004 | Thulasidas |
| 2006/0136744 A1* | 6/2006 | Lange ................ G06K 9/00536 |
| | | 713/186 |
| 2006/0293606 A1 | 12/2006 | Tomita |
| 2009/0074259 A1* | 3/2009 | Baltatu ................ G06K 9/6284 |
| | | 382/118 |
| 2012/0165633 A1 | 6/2012 | Khair |
| 2014/0142451 A1 | 5/2014 | Kim et al. |
| 2014/0188770 A1 | 7/2014 | Agrafioti et al. |

FOREIGN PATENT DOCUMENTS

| | | |
|---|---|---|
| KR | 10-1270954 B1 | 6/2013 |
| KR | 10-2013-0140439 A | 12/2013 |
| WO | WO 2012/151680 A1 | 11/2012 |

* cited by examiner

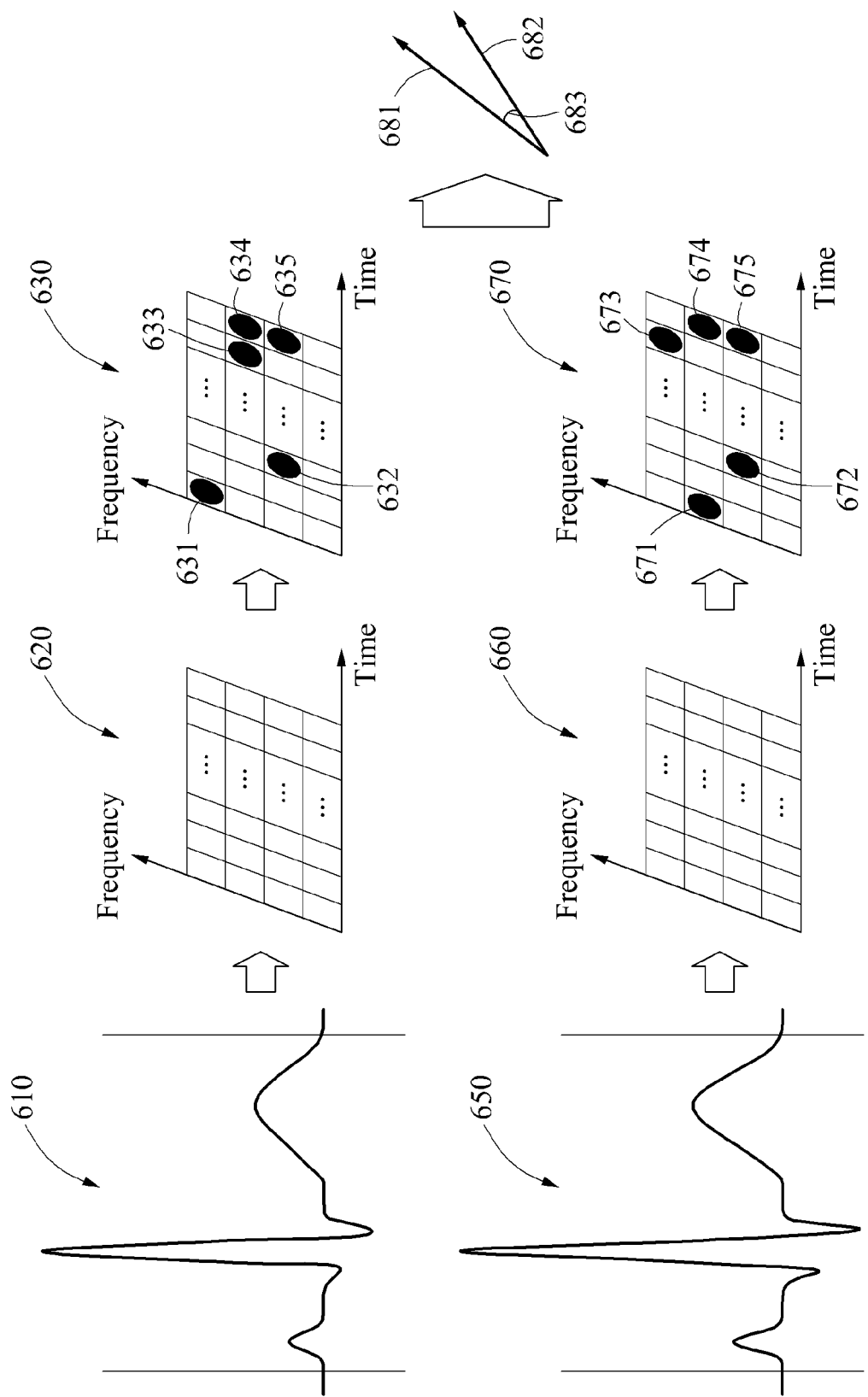

METHOD AND APPARATUS FOR AUTHENTICATING USER BASED ON BIOSIGNAL

CROSS-REFERENCE TO RELATED APPLICATION(S)

This application claims the benefit under 35 USC 119(a) of Korean Patent Application No. 10-2014-0194107, filed on Dec. 30, 2014, in the Korean Intellectual Property Office, the entire disclosure of which is incorporated herein by reference for all purposes.

BACKGROUND

1. Field

The following description relates to a method and apparatus for authenticating a user based on a biosignal.

2. Description of Related Art

Recently, technologies that utilize various signals and data from human body are being developed. For example, biometric technology for establishing an identity of a person based on his or her biosignal or other biometric data for security purpose is gaining attention. Biometric technology may refer to technology for extracting a physiological or biological signal or data associated with a user and comparing the extracted signal or data to pre-stored data, thereby authenticating the user as a registered user through identification. As an example, technology for recognizing a user based on a personal electrocardiogram (ECG) signal is under development in a field of biometric technology.

Biometric technology capitalizes in the fact that certain biosignals are unique to each user. Because these unique biosignals are not easily stolen or accidentally lost and are robust against forgery or falsification, the application of biometric technology in security technology appears to be promising.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an authentication apparatus includes a data set generator configured to generate an authentication data set by extracting waveforms from a biosignal of a user; a similarity calculator configured to match each of the extracted waveforms to registered waveforms included in a registration data set stored in a memory, and calculate a similarity between each of the extracted waveforms and the registered waveforms; an auxiliary similarity calculator configured to extract a representative authentication waveform indicating a representative waveform of the extracted waveforms and a representative registration waveform indicating a representative waveform of the registered waveforms, and calculate a similarity between the representative authentication waveform and the representative registration waveform; and an authenticator configured to authenticate the user based on the similarity between each of the extracted waveforms and the registered waveforms and the similarity between the representative authentication waveform and the representative registration waveform.

The biosignal may include an electrocardiogram (ECG) signal.

The memory may be configured to store the registration data set including the registered waveforms extracted from a biosignal of a user during a registration before the data set generator generates the authentication data set.

The similarity calculator may be configured to extract a feature of each of the extracted waveforms and a feature of each of the registered waveforms, and calculate a similarity between the feature of each of the extracted waveforms and the feature of each of the registered waveforms.

The similarity calculator may be configured to convert each of the extracted waveforms into a feature vector and the registered waveforms into a feature vectors, and calculate a similarity between the feature vector into which each of the extracted waveforms is converted and each of the feature vectors into which the registered waveforms are converted.

The similarity calculator may be configured to change dimensions of each of the extracted waveforms and the registered waveforms, to convert each of the extracted waveforms into the feature vector and the registered waveforms into the feature vectors.

The similarity calculator may be configured to extract a feature parameter of each of the extracted waveforms and a feature parameter of each of the registered waveforms, and calculate a similarity between the feature parameter of each of the extracted waveforms and the feature parameter of each of the registered waveforms.

The feature parameters may include at least one of a PR interval, a PR segment, a QRS complex, an ST segment, an ST interval, a QT interval, an RR interval, an amplitude, and noise power of each of the registered waveforms or the extracted waveforms.

The auxiliary similarity calculator may be configured to extract a feature of the representative extracted waveform and a feature of the representative registration waveform, and calculate a similarity between the feature of the representative authentication waveform and the feature of the representative registration waveform.

The auxiliary similarity calculator may be configured to convert the representative authentication waveform and the representative registration waveform into feature vectors, and calculate a similarity between the feature vector into which the representative authentication waveform is converted and the feature vector into which the representative registration waveform is converted.

The auxiliary similarity calculator may be configured to extract a feature parameter of the representative authentication waveform and a feature parameter of the representative registration waveform, and calculate a similarity between the feature parameter of the representative authentication waveform and the feature parameter of the representative registration waveform.

The authenticator may be configured to determine whether the user matches a user of the registration data set based on the similarity between the feature of the representative authentication waveform and the feature of the representative registration waveform and a similarity between each of the extracted waveforms and each of the registered waveforms.

The authenticator may be configured to normalize the similarity between the feature of the representative authentication waveform and the feature of the representative registration waveform and the similarity between each of the extracted waveforms and each of the registered waveforms.

The authenticator may be configured to determine whether the user matches the user of the registration data set by setting a different weight to each of the similarity between the feature of the representative authentication waveform and the feature of the representative registration waveform and the similarity between each of the extracted waveforms and each of the registered waveforms.

The authenticator may be configured to determine whether the extracted waveforms corresponds to the registered waveforms by applying, to a classifier, the similarity between the feature of the representative authentication waveform and the feature of the representative registration waveform and the similarity between each of the extracted waveforms and each of the registered waveforms.

The classifier may include at least one of a support vector machine (SVM) and a nearest neighbor (NN).

Operations of the data set generator, the similarity calculator, and the auxiliary similarity calculator may be iterated in response to the authenticator determining that the user differs from a user of the registration data set.

The authenticator may be configured to determine that the user differs from the user of the registration data set in response to the operations of the data set generator, the similarity calculator, and the auxiliary similarity calculator iterated a number of times greater than a predetermined threshold.

In another general aspect, an authentication apparatus may include a sensor configured to detect a biosignal of a user, and a processor configured to generate an authentication data set by extracting waveforms from a biosignal of a user, match each of the extracted waveforms to registered waveforms included in a registration data set that is stored in a memory, calculate a similarity between each of the extracted waveforms and the registered waveforms, extract a representative authentication waveform indicating a representative waveform of the extracted waveforms and a representative registration waveform indicating a representative waveform of the registered waveforms, calculate a similarity between the representative authentication waveform and the representative registration waveform, and authenticate the user based on the similarity between each of the extracted waveforms and the registered waveforms and the similarity between the representative authentication waveform and the representative registration waveform.

The biosignal may include an electrocardiogram (ECG) signal.

The processor may be configured to extract a feature of each of the extracted waveforms and a feature of each of the registered waveforms, and calculate a similarity between the feature of each of the extracted waveforms and the feature of each of the registered waveforms.

The processor may be configured to extract a feature of the representative authentication waveform and a feature of the representative registration waveform, and calculate a similarity between the feature of the representative authentication waveform and the feature of the representative registration waveform.

In another general aspect, an authentication method involves generating an authentication data set by extracting waveforms from a biosignal of a user, match each of the extracted waveforms to each of registered waveforms included in a registration data set that is stored in a memory and calculating a similarity between each of the extracted waveforms and the registered waveforms, extracting a representative authentication waveform indicating a representative waveform of the extracted waveforms and a representative registration waveform indicating a representative waveform of the registered waveforms and calculating a similarity between the representative authentication waveform and the representative registration waveform, and authenticating the user based on the similarity between each of the extracted waveforms and the registered waveforms and the similarity between the representative authentication waveform and the representative registration waveform.

In yet another general aspect, there is provided a non-transitory computer-readable storage medium storing therein a program comprising instructions to cause a computer to perform the general aspect of the method described above.

In another general aspect, an authentication apparatus includes a sensor configured to detect a biosignal, and a processor configured to extract waveforms from the detected biosignal, calculate a similarity of each of the extracted waveforms to each of registered waveforms included in a memory, extract a representative authentication waveform based on the extracted waveforms and a representative registration waveform based on the registered waveforms, calculate a similarity between the representative authentication waveform and the representative registration waveform, and determine whether an owner of the extracted waveforms matches an owner of the registered waveform based on the similarity of each of the extracted waveforms to the registered waveforms and the similarity of the representative authentication waveform to the representative registration waveform.

The sensor may include an electrode configured to measure an electrocardiogram signal of a user.

The processor may be configured to extract a feature parameter of each of the extracted waveforms and a feature parameter of each of the registered waveforms, the feature parameters comprising at least one of a PR interval, a PR segment, a QRS complex, an ST segment, an ST interval, a QT interval, an RR interval, an amplitude, and noise power of each of the registered waveforms or the extracted waveforms.

Other features and aspects will be apparent from the following detailed description, the drawings, and the claims.

BRIEF DESCRIPTION OF THE DRAWINGS

FIG. 6 is a block diagram illustrating an example of a method of calculating a similarity between an extracted waveform and a registered waveform.

Figure 1A:
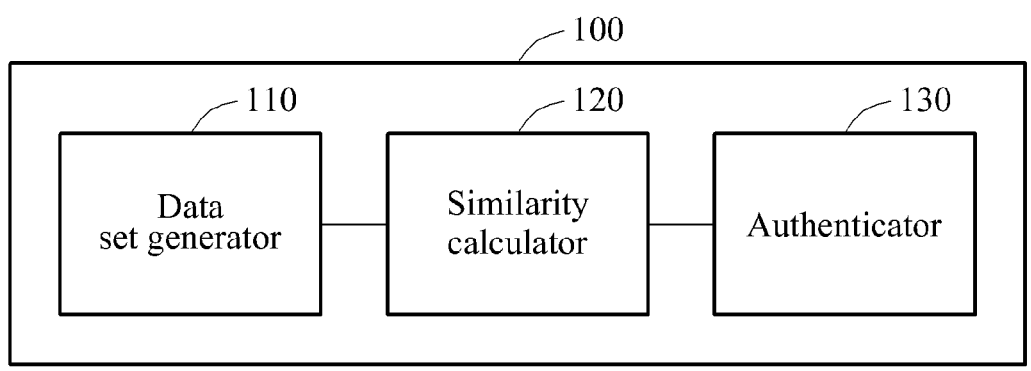
FIG. 1A is a block diagram illustrating an example of an authentication apparatus.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Hereinafter, example embodiments will be described in detail with reference to the accompanying drawings.

It should be understood, however, that there is no intent to limit this disclosure to the particular example embodiments disclosed. On the contrary, example embodiments are to cover all modifications, equivalents, and alternatives falling within the scope of the example embodiments.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "include" and/or "have," when used in this specification, specify the presence of stated features, integers, steps, operations, elements, components or combinations thereof, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

FIG. 1A illustrates an example of an authentication apparatus 100.

Referring to FIG. 1A, the authentication apparatus 100 includes a data set generator 110, a similarity calculator 120, and an authenticator 130. The data set generator 110, the similarity calculator 120 and the authenticator 130 may include one or more processors or memories [LC1].

The data set generator 110 generates an authentication data set by extracting a plurality of waveforms for authenticating a user from a biosignal of the user and stores the generated authentication data set in a memory. The biosignal may refer to a signal detected from a body and include, for example, an electrocardiogram (ECG) signal, an electroencephalogram (EEG) signal, an electromyogram (EMG) signal, and an electrooculogram (EOG) signal. Also, the biosignal may include other biosignals as well as the foregoing. The data set generator 110 may receive the biosignal from a sensor, which is a hardware device. Examples of the sensor include an ECG sensor, an EEG sensor, an EMG sensor, an EOG sensor and the like. However, the present disclosure is not limited thereto. Other sensors that measure a biosignal or data regarding the user may be used in another example. In this example, the sensor may be included in the authentication apparatus 100, or may be an external apparatus different from the authentication apparatus 100. Also, the authentication apparatus 100 may receive the biosignal from a sensor included in a wearable device and a sensor included in a mobile device as well as a sensor used for a medical instrument.

Hereinafter, the following descriptions will be provided based on the ECG signal for increased conciseness and clarity. However, a type of the biosignal is not limited thereto. Alternatively, the present disclosure is also applicable to various biosignals.

In this example, the ECG sensor may include a plurality of electrodes, an amplifier, and a digital filter. The plurality of electrodes may be configured to contact the skin of a user such as, for example, a finger tip, in order to detect the ECG signal of the user. The amplifier may amplify the ECG signal detected in the electrodes. In this example, the amplifier may be expressed as an analog front-end (AFE). The digital filter may convert the amplified ECG signal into a digital signal. Through this, a signal-to-noise ratio (SNR) of the ECG signal may be enhanced.

In another example, the ECG sensor may detect the ECG signal of the user using a plurality of electrodes.

Figure 1B:
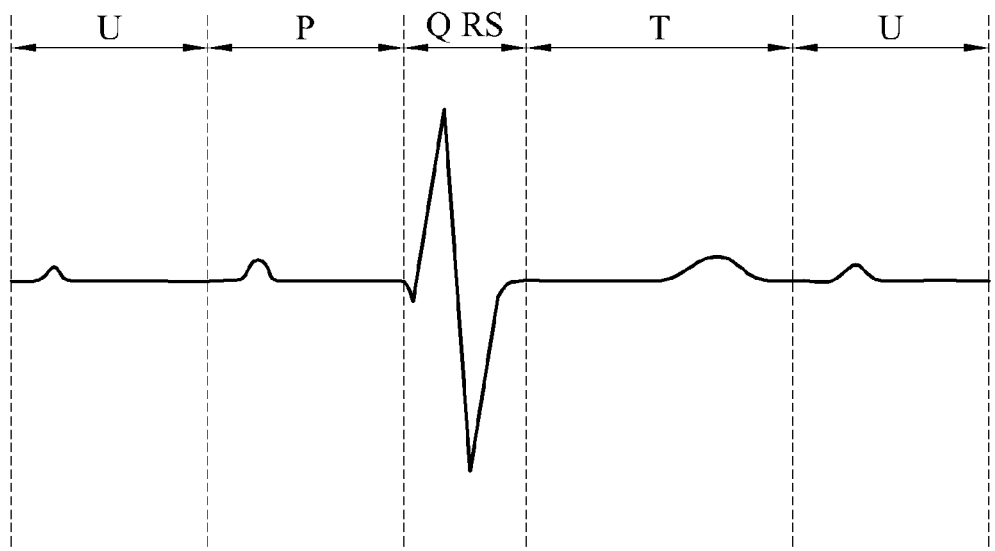
FIG. 1B is a waveform showing an example of an ECG signal.

The data set generator 110 may extract a plurality of waveforms for use in an authentication. The data set generator 110 may divide the ECG signal based on a heart rate and extract a set of waveforms, including a P wave, a QRS wave, a T wave, and a U wave, for example [LC2]. Examples of a P wave, a QRS wave, a T wave and a U wave are illustrated in FIG. 1B. Also, the data set generator 110 may not extract a waveform having a quality value less than a predetermined quality value, as an authentication waveform by assessing a quality of an extracted waveform.

In an example, the data set generator 110 may perform a preprocessing procedure to remove dominant noise from the plurality of extracted authentication waveforms. For example, in the preprocessing procedure, the data set generator 110 may extract a plurality of extracted authentication waveforms between 0.5 and 40 hertz (Hz) from the plurality of extracted authentication waveforms. Also, the data set generator 110 may remove dominant noise such as a motion artifact, power noise, for example, an ECG waveform of a frequency band between 50 and 60 Hz, and a direct current (DC) baseline deviating from the plurality of extracted authentication waveforms.

The data set generator 110 may align the plurality of extracted authentication waveforms based on an R peak.

The data set generator 110 may incorporate the extracted authentication waveforms in the authentication data set. The authentication data set may refer to a data set including a user authentication waveform used to authenticate a corresponding user. According to one example, the authentication data set may be a probe data set obtained from a probe [LC3]. The authentication data set may accumulate an ECG waveform of the corresponding user in the authentication data set and may also remove the authentication data set when the authenticating is terminated.

The authentication apparatus 100 may further include a memory storage (not shown). The storage may store, in advance, a registration data set including a plurality of waveforms extracted from a biosignal of a preregistered user during a registration. The registration data set may refer to a data set including user registration waveforms used to register the corresponding user. In an example, the authentication apparatus 100 may acquire a biosignal of a user attempting to be registered and extract a plurality of waveforms to register the user from the acquired biosignal, thereby generating a registration data set. Also, the authentication apparatus 100 may generate a registration data set by extracting a plurality of waveforms from a biosignal of a user that is stored in the authentication apparatus 100 prior to performing the authentication. In another example, the authentication apparatus 100 may receive a registration data set from an external apparatus.

The similarity calculator 120 performs one-to-one matching on each of the plurality of extracted waveforms included in the authentication data set to the plurality of registered waveforms included in the registration data set and calculate a similarity between each of the extracted waveforms and the registered waveforms. For example, the similarity calculator 120 may calculate the similarity by matching the authentication data set and the registration data set. As an example, when M extracted waveforms are included in the authentication data set, and when N registered waveforms are included in the registration data set, the similarity calculator 120 may perform matching M*N times to calculate a similarity between each of the M extracted waveforms and each of the N registered waveforms. Also, the similarity calculator 120 may generate M*N histograms, each indicating the similarity between each of the M extracted waveforms and each of the N registered waveforms.

The similarity calculator 120 may perform one-to-one matching on all extracted waveforms included in the authentication data set to all registered waveforms included in the registration data set in lieu of extracting a representative authentication waveform from the extracted waveforms and extracting a representative registration waveform from the registered waveforms. Through this, a data loss occurring in a process of extracting the representative authentication waveform or the representative registration waveform may be prevented, and an influence on a user authentication affected by a waveform having a relatively high irregularity among waveforms included in the authentication data set or the registration data set may be reduced. As an example, among four extracted authentication waveforms included in an authentication data set, one waveform may include a relatively large amount of noise. In this example, a representative authentication waveform extracted from the four extracted authentication waveforms may be distorted due to the one waveform. In lieu of extracting the representative authentication waveform from the four authentication waveforms, the similarity calculator 120 may perform matching on each of the four extracted authentication waveforms to each of a plurality of registered waveforms included in a registration data set, thereby reducing an authentication error occurring due to the one waveform.

To calculate the similarity, the similarity calculator 120 may extract a feature of each of the extracted authentication waveforms and a feature of each of the registered waveforms. The feature may refer to an attribute of a waveform, and may also be expressed as a feature point. In an example, the feature may include a feature vector and a feature parameter. However, the disclosure is not limited thereto. Instead, the feature may include all configurations indicating the attribute of the waveform.

In an example, the similarity calculator 120 may convert each of the registered waveforms and extracted authentication waveforms into a feature vector. The similarity calculator 120 may convert each of the registered waveforms and extracted authentication waveforms into the feature vector by changing a dimension of each of the registered waveforms and extracted authentication waveforms. As an example, the similarity calculator 120 may convert each of the registered waveforms and extracted authentication waveforms into a frequency domain based on, for example, an auto-correction/discrete cosine transform (AC/DCT), a short-time Fourier transform (STFT), a mel-frequency cepstral coefficient (MFCC), a wavelet, a linear predictive coding/linear predictive spectrum coefficient (LPC/LPCC), and a line spectrum pair (LSP). The similarity calculator 120 may reduce the dimension of each of the registered waveforms and extracted authentication waveforms by selecting a feature component of each of the registered waveforms and extracted authentication waveforms converted into the frequency domain based on, for example, a principle component analysis (PCA), a linear discriminative analysis (LDA), and an eigenfeature regularization and extraction (ERE). The similarity calculator 120 may generate the feature vector based on each of the registered waveforms and extracted authentication waveforms of which the dimension is reduced.

In an example, the similarity calculator 120 may extract a feature parameter of each of the extracted authentication waveforms and a feature parameter of each of the registered waveforms. The feature parameter may include at least one of a PR interval, a PR segment, a QRS complex, an ST segment, an ST interval, a QT interval, an RR interval, an amplitude, and noise power of an ECG waveform.

The similarity calculator 120 may calculate a similarity between the feature of each of the extracted authentication waveforms and the feature of each of the registered waveforms. As an example, the similarity calculator 120 may extract a similarity between each of a plurality of feature vectors into which a plurality of extracted authentication waveforms is converted and each of a plurality of feature vectors into which a plurality of registered waveforms is converted, or a similarity between a feature parameter of each of the extracted authentication waveforms and a feature parameter of each of the registered waveforms, based on, for example, a correlation, a cosine similarity, a Euclidean distance, an L1-norm, a P-norm, and a root-mean-square error (RMSE). In this example, the similarity may increase according to an increase in the correlation or the cosine similarity. Conversely, the similarity may decrease according to a decrease in a value of the RMSE or the Euclidean distance. Also, in addition to the foregoing, the similarity calculator 120 may extract the similarity between the feature of each of the extracted authentication waveforms and the feature of each of the registered waveforms based on any feature comparison scheme.

In an example, the similarity calculator 120 may express the similarity between the feature of each of the extracted authentication waveforms and the feature of each of the registered waveforms in a form of a histogram, a feature vector, or a value.

The authenticator 130 authenticates the user based on a similarity. The authenticator 130 may determine whether the user matches a user of the registration data set based on a similarity between each of the extracted authentication waveforms and each of the registered waveforms.

In an example, to perform an authentication, the authenticator 130 may normalize the similarity between each of the extracted authentication waveforms and each of the registered waveforms. In this example, the authenticator 130 may normalize the similarity based on normalizing functions such as a min-max, a Tan h-estimator, a z-score, and the like.

The authenticator 130 may apply, to a classifier (not shown), the similarity between each of the extracted authentication waveforms and each of the registered waveforms to determine whether the extracted authentication waveforms correspond to the registered waveforms. In response to a determination that the extracted authentication waveforms correspond to the registered waveforms, the authenticator 130 may authenticate the user of the authentication data set matches the user of the registration data set. In response to a determination that the extracted authentication waveforms do not correspond to the registered waveforms, the authenticator 130 may determine that the user of the authentication data set differs from the user of the registration data set.

As an example, the classifier may be one of a support vector machine (SVM) and a nearest neighbor (NN), and the authenticator 130 may apply, to one of the SVM and the NN, the similarity between each of the extracted authentication waveforms and each of the registered waveforms to determine whether the extracted authentication waveforms correspond to the registered waveforms.

When the authenticator 130 determines that the extracted authentication waveforms do not correspond to the registered waveforms, the authentication apparatus 100 may iterate operations of the data set generator 110, the similarity calculator 120, and the authenticator 130. For example, when the authenticator 130 determines that the extracted authentication waveforms do not correspond to the registered waveforms, the data set generator 110 may reacquire an ECG signal of the user attempting to be authenticated and extract a plurality of authentication waveforms from the required ECG signal, thereby generating a new authentication data set. The similarity calculator 120 may perform one-to-one matching on each of the authentication waveforms included in the new authentication data set to the plurality of registered waveforms included in the registration data set, and calculate a similarity between each of the newly extracted authentication waveforms and the registered waveforms. The authenticator 130 may authenticate the user based on the calculated similarity. In this example, the authenticator 130 may determine that the user differs from the user of the registration data set when the operations of the data set generator 110, the similarity calculator 120, and the authenticator 130 are iterated a number of times greater than a predetermined threshold.

Through the operations of the data set generator 110, the similarity calculator 120, and the authenticator 130, the authentication apparatus 100 may prevent the data loss occurring in a process of extracting the representative authentication waveform or the representative registration waveform, and reduce a false acceptance rate (FAR) and a false rejection rate (FRR) by reducing the influence on the user authentication affected by the waveform having a relatively high peculiarity among the waveforms included in the authentication data set or the registration data set.

Figure 2:
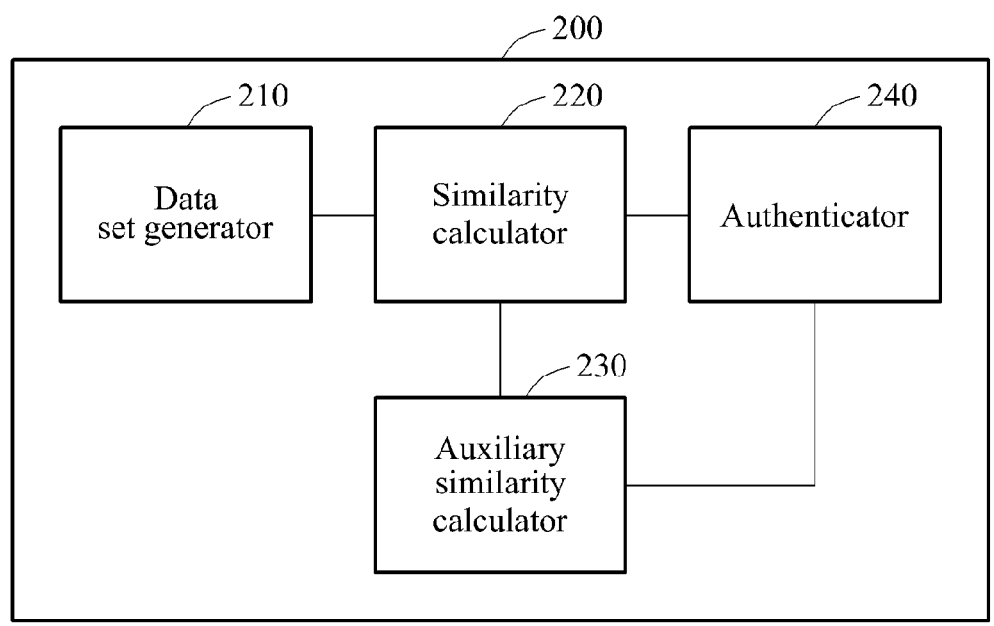
FIG. 2 is a block diagram illustrating another example of an authentication apparatus.

FIG. 2 illustrates an example of an authentication apparatus 200.

Referring to FIG. 2, the authentication apparatus 200 includes a data set generator 210, a similarity calculator 220, an auxiliary similarity calculator 230, and an authenticator 240. The data set generator 210, the similarity calculator 220, the auxiliary similarity calculator 230, and the authenticator 240 may include one or more processors or memories.

The data set generator 210 generates an authentication data set by extracting a plurality of waveforms for authenticating a user from a biosignal of the user.

The similarity calculator 220 performs one-to-one matching on each of the plurality of extracted authentication waveforms included in the authentication data set to a plurality of registered waveforms included in a registration data set, and calculates a similarity between each of the extracted authentication waveforms and the registered waveforms.

Since the descriptions provided with reference to the data set generator 110 and the similarity calculator 120 of FIG. 1A are also applicable here, repeated descriptions with respect to the data set generator 210 and the similarity calculator 220 of FIG. 2 will be omitted for increased clarity and conciseness.

The auxiliary similarity calculator 230 extracts a representative authentication waveform of the authentication data set and a representative registration waveform of the registration data set, and extracts a similarity between the representative authentication waveform and the representative registration waveform. The representative authentication waveform may refer to, for example, a representative waveform of the extracted authentication waveforms, and the representative registration waveform, may refer to, for example, a representative waveform of the registered waveforms. As an example, the auxiliary similarity calculator 230 may generate the representative authentication waveform by calculating an average value of the extracted authentication waveforms, and may generate the representative registration waveform by calculating an average value of the registered waveforms. However, the disclosure is not limited thereto. Alternatively, the auxiliary similarity calculator 230 may extract the representative authentication waveform and the representative registration waveform based on various statistical methods.

The auxiliary similarity calculator 230 may extract a feature of the representative authentication waveform and a feature of the representative registration waveform.

In an example, the auxiliary similarity calculator 230 may convert the representative authentication waveform and the representative registration waveform into feature vectors. The auxiliary similarity calculator 230 may change dimensions of the representative authentication waveform and the representative registration waveform to convert the representative authentication waveform and the representative registration waveform into the feature vectors. As an example, the auxiliary similarity calculator 230 may convert the representative authentication waveform and the representative registration waveform into frequency domains based on, for example, an AC/DCT, an SIFT, an MFCC, a wavelet, an LPC/LPCC, and an LSP. The auxiliary similarity calculator 230 may reduce the dimensions of the representative authentication waveform and the representative registration waveform by selecting feature components of the representative authentication waveform and the representative registration waveform converted into the frequency domains based on, for example, a PCA, an LDA, and an ERE. The auxiliary similarity calculator 230 may generate the feature vectors based on the representative authentication waveform and the representative registration waveform of which the dimensions are reduced.

In an example, the auxiliary similarity calculator 230 may extract a feature parameter of the representative authentication waveform and a feature parameter of the representative registration waveform. For example, the auxiliary similarity calculator 230 may extract, as the feature parameters, at least one of a PR interval, a PR segment, a QRS complex, an ST segment, an ST interval, a QT interval, an RR interval, an amplitude, and noise power of the representative authentication waveform and the representative registration waveform.

The auxiliary similarity calculator 230 may calculate a similarity between the feature of the representative authentication waveform and the feature of the representative registration waveform. As an example, the auxiliary similarity calculator 230 may calculate a similarity between the feature vector into which the representative authentication waveform is converted and the feature vector into which the representative registration waveform is converted or a similarity between the feature parameter of the representative authentication waveform and the feature parameter of the representative registration waveform, based on, for example, a correlation, a cosine similarity, a Euclidean distance, an L1-norm, a P-norm, and an RMSE. Also, in addition to the foregoing, the auxiliary similarity calculator 230 may extract the similarity between the feature of the representative authentication waveform and the feature of the representative registration waveform based on any feature comparison scheme.

In an example, the auxiliary similarity calculator 230 may express the similarity between the feature of the representative authentication waveform and the feature of the representative registration waveform in a form of a histogram, a feature vector, or a value.

The authenticator 240 may determine whether the user matches a user of the registration data set based on a similarity between each of the extracted authentication waveforms and each of the registered waveforms and the similarity between the representative authentication waveform and the representative registration waveform.

In an example, to perform an authentication, the authenticator 240 may normalize the similarity between each of the authentication waveforms and each of the registered waveforms and the similarity between the representative authentication waveform and the representative registration waveform based on normalizing functions such as a min-max, a Tan h-estimator, a z-score, and the like.

Also, the authenticator 240 may authenticate the user by setting a different weight to each of the similarity between each of the extracted authentication waveforms and each registered waveforms and the similarity between the representative authentication waveform and the representative registration waveform. For example, the authenticator 240 may set a weight in advance, or set the weight by comparing the similarity between each of the extracted authentication waveforms and each of the registered waveforms and the similarity between the representative authentication waveform and the representative registration waveform. As an example, the authenticator 240 may assign a greater weight to a similarity having a greater value between an average of the similarity between each of the extracted authentication waveforms and each of the registered waveforms and the similarity between the representative authentication waveform and the representative registration waveform, and assign a smaller weight to a similarity having a smaller value therebetween.

In an example, the authenticator 240 may apply, to a classifier (not shown), the similarity between each of the extracted authentication waveforms and each of the registered waveforms and the similarity between the representative authentication waveform and the representative registration waveform to determine whether the extracted authentication waveforms correspond to the registered waveforms. As an example, the classifier may be one of an SVM and an NN. In response to a determination that the extracted authentication waveforms correspond to the registered waveforms, the authenticator 240 may authenticate the user of the authentication data set matching the user of the registration data set. In response to a determination that the extracted authentication waveforms do not correspond to the registered waveforms, the authenticator 240 may determine that the user of the authentication data set differs from the user of the registration data set. During a user authentication, an FAR and an FRR may be reduced by applying, to the classifier, the similarity between the representative authentication waveform and the representative registration waveform in addition to the similarity between each of the extracted authentication waveforms and each of the registered waveforms.

When the authenticator 240 determines that the extracted authentication waveforms do not correspond to the registered waveforms, the authentication apparatus 200 may iterate operations of the data set generator 210, the similarity calculator 220, the auxiliary similarity calculator 230, and the authenticator 240. In this example, the authenticator 240 may determine that the user differs from the user of the registration data set when the operations of the data set generator 210, the similarity calculator 220, the auxiliary similarity calculator 230, and the authenticator 240 are iterated a greater number of times than a predetermined threshold.

Figure 3:
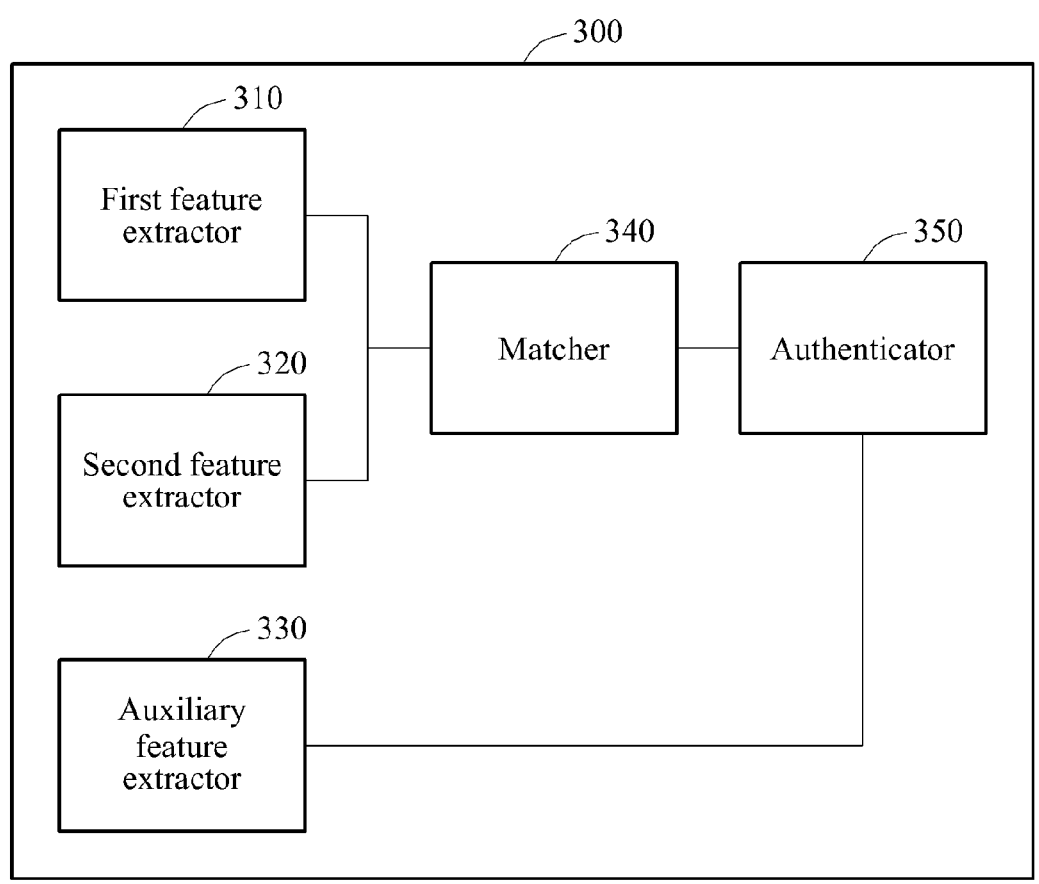
FIGS. 3 and 4 are block diagrams illustrating still another example of an authentication apparatus.
Figure 4:
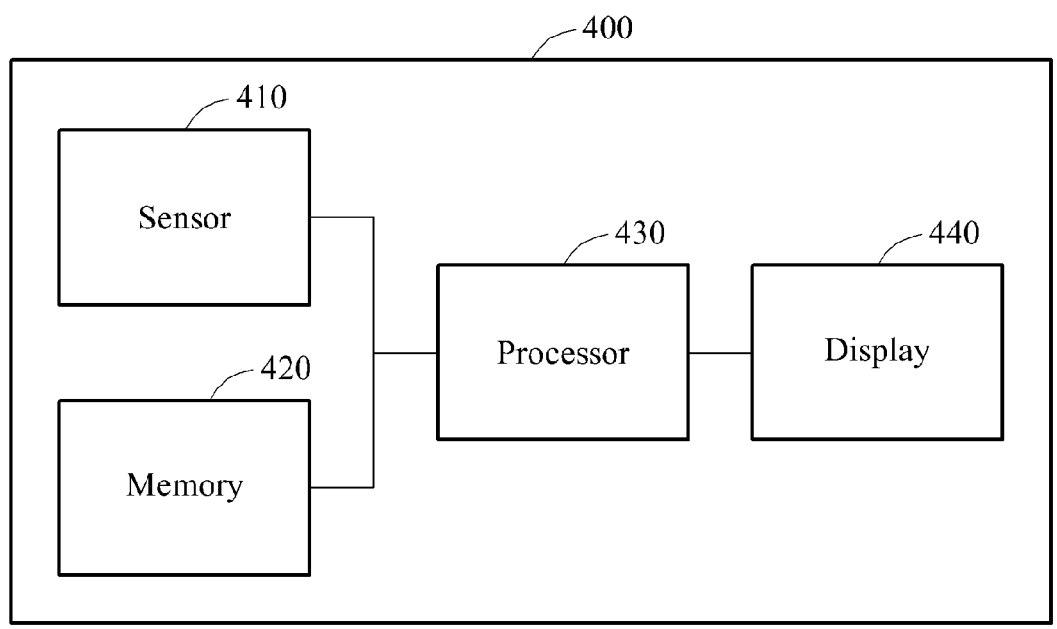

FIG. 3 illustrates an example of an authentication apparatus 300, and FIG. 4 illustrates another example of an authentication apparatus 400.

Referring to FIG. 3, the authentication apparatus 300 includes a first feature extractor 310, a second feature extractor 320, an auxiliary feature extractor 330, a matcher 340, and an authenticator 350. The first feature extractor 310, the second feature extractor 320, the auxiliary feature extractor 330, the matcher 340, and the authenticator 350 may include one or more processors or memories.

In an example, the authentication apparatus 300 may operate based on an operation mode. The operation mode may include a registration mode and a normal mode. In the registration mode, the authentication apparatus 300 may perform an operation of registering a biosignal of a registration user. The registration user may refer to, for example, a user attempting to be authenticated. In the authentication mode, the authentication apparatus 300 may perform an operation of authenticating an authentication user as a registered user based on a biosignal of the authentication user. The authentication user may refer to, for example, a user attempting to be authenticated.

Hereinafter, the authentication apparatus 300 operating in the authentication mode will be explained with reference to the following descriptions.

The first feature extractor 310 may extract a feature of a plurality of registered waveforms extracted from an ECG signal of the registered user. The first feature extractor 310 may extract the plurality of registered waveforms from the ECG signal of the registered user acquired in the registration mode. The first feature extractor 310 may extract a P wave, a QRS wave, a T wave, and a U wave as one registered waveform by dividing the ECG signal based on a heart rate. The first feature extractor 310 may incorporate the one registered waveform and/or the extracted registered waveforms in a registration data set.

Also, the first feature extractor 310 may extract a feature for each of the plurality of registered waveforms. As an example, the first feature extractor 310 may extract a feature vector or a feature parameter for each of the plurality of registered waveforms.

The second feature extractor 320 may extract a feature of a plurality of extracted authentication waveforms extracted from an ECG signal of the authentication user. The second feature extractor 320 may extract the plurality of extracted authentication waveforms from the ECG signal of the authentication user acquired in the authentication mode. The second feature extractor 320 may extract a P wave, a QRS wave, a T wave, and a U wave as one authentication waveform by dividing the ECG signal based on a heart rate. The second feature extractor 320 may incorporate the extracted authentication waveforms in a registration data set.

Also [LC4], the second feature extractor 320 may extract a feature, for example, a feature vector and a feature parameter, for each of the plurality of extracted authentication waveforms.

Although FIG. 3 illustrates the first feature extractor 310 is disposed separate from the second feature extractor 320, each of the first feature extractor 310 and the second feature extractor 320 may be provided as an independent unit separate from one another, and the first feature extractor 310 and the second feature extractor 320 may also be included in a single unit.

The matcher 340 may perform one-to-one matching on the feature of each of the extracted authentication waveforms and the feature of each of the registered waveforms, and calculate a similarity between the feature of each of the extracted authentication waveforms and the feature of each of the registered waveforms. When M extracted authentication waveforms are provided, and when N registered waveforms are included in the registration data set, the matcher 340 may perform matching M*N times to calculate M*N similarities.

As an example, the matcher 340 may extract a similarity between each of a plurality of feature vectors into which the plurality of extracted authentication waveforms is converted and each of a plurality of feature vectors into which the plurality of registered waveforms is converted, or a similarity between a feature parameter of each of the extracted authentication waveforms and a feature parameter of each of the registered waveforms, based on, for example, a correlation, a cosine similarity, a Euclidean distance, an L1-norm, a P-norm, and an RMSE.

The auxiliary feature extractor 330 may extract a representative registration waveform of the plurality of registered waveforms included in the registration set and extract a representative authentication waveform of the plurality of extracted authentication waveforms included in the authentication data set, thereby extracting a similarity between the representative registration waveform and the representative authentication waveform. In an example, the auxiliary feature extractor 330 may extract the representative registration waveform by calculating an average value of the registered waveforms, and extract the representative authentication waveform by calculating an average value of the extracted authentication waveforms. The auxiliary feature extractor 330 may extract a feature, for example, a feature vector and a feature parameter, of the representative authentication waveform and a feature of the representative registration waveform.

Also, the auxiliary feature extractor 330 may calculate the similarity between the feature of the representative authentication waveform and the feature of the representative registration waveform. Since the registration data set includes one representative registration waveform and the authentication data set includes one representative authentication waveform, the auxiliary feature extractor 330 may calculate one similarity. As an example, the auxiliary feature extractor 330 may calculate a similarity between a feature vector of the representative authentication waveform and a feature vector of the representative registration waveform or a similarity between a feature parameter of the representative authentication waveform and a feature parameter of the representative registration waveform, based on, for example, a correlation, a cosine similarity, a Euclidean distance, an L1-norm, a P-norm, and an RMSE.

The authenticator 350 may determine whether a user matches a user of the registration data set based on the similarity between each of the extracted authentication waveforms and each of the registered waveforms and the similarity between the representative authentication waveform and the representative registration waveform.

In an example, the authenticator 350 may normalize the similarity between each of the extracted authentication waveforms and each of the registered waveforms and the similarity between the representative authentication waveform and the representative registration waveform, and may set a different weight to each of the similarity between the representative authentication waveform and the representative registration waveform and the similarity between each of the extracted authentication waveforms and each of the registered waveforms.

The authenticator 350 may apply, to a classifier (not shown), the similarity between the representative authentication waveform and the representative registration waveform and the similarity between each of the extracted authentication waveforms and each of the registered waveforms, thereby determining whether the registered waveforms correspond to the extracted authentication waveforms. The classifier may be, for example, an SVM and an NN.

In response to a determination that the registered waveforms correspond to the extracted authentication waveforms, the authenticator 350 may authenticate the user of the authentication data set matching the user of the registration data set. In response to a determination that the registered waveforms do not correspond to the extracted authentication waveforms, the authenticator 350 may determine that the user of the authentication data set differs from the user of the registration data set.

In another example, the authenticator 350 may apply the similarity between each of the extracted authentication waveforms and each of the registered waveforms and then, apply the similarity between the representative authentication waveform and the representative registration waveform to the classifier. Alternatively, the authenticator 350 may apply the similarity between the representative authentication waveform and the representative registration waveform and then, apply the similarity between each of the extracted authentication waveforms and each of the registered waveforms to the classifier. As an example, the authenticator 350 may apply the similarity between each of the extracted authentication waveforms and each of the registered waveforms to the classifier, and determine whether the registered waveforms correspond to the extracted authentication waveforms. In response to a determination that the registered waveforms correspond to the extracted authentication waveforms, the authenticator 350 may apply the similarity between the representative authentication waveform and the representative registration waveform to the classifier and determine whether the representative registration waveform corresponds to the representative authentication waveform. In this example, when it is determined that the registered waveforms do not correspond to the extracted authentication waveforms as a result of the applying of the similarity between each of the extracted authentication waveforms and each of the registered waveforms to the classifier, the authenticator 350 may determine that the user differs from the user of the registration data set.

As another example, the authenticator 350 may apply the similarity between the representative authentication waveform and the representative registration waveform to the classifier and determine whether the representative registration waveform corresponds to the representative authentication waveform. In response to a determination that the representative registration waveform corresponds to the representative authentication waveform, the authenticator 350 may apply the similarity between each of the extracted authentication waveforms and each of the registered waveforms to the classifier, and determine whether the registered waveforms correspond to the extracted authentication waveforms. In response to a determination that the registered waveforms correspond to the extracted authentication waveforms, the authenticator 350 may authenticate the user matching the user of the registration data set.

During a user authentication, an FAR and an FRR may be reduced by applying the similarity between the representative authentication waveform and the representative registration waveform in addition to the similarity between each of the extracted authentication waveforms and each of the registered waveforms.

Referring to FIG. 4, the authentication apparatus 400 includes a sensor 410, a memory 420, a processor 430, and a display 440. The sensor 410, the memory 420, the processor 430 and the display each include one or more hardware components.

In this example, the sensor 410 includes an ECG sensor, an EEG sensor, an EMG sensor, and/or an EOG sensor. However, in another example, the sensor 410 may include other sensors used to extract a signal detected from a body. When the sensor 410 includes the ECG sensor, the ECG sensor may measure an ECG waveform of a user using a first electrode, a second electrode, and a third electrode. In an example, the ECG sensor may include the first electrode through the third electrode, an amplifier, and a digital converter. The first electrode through the third electrode may be in contact with a skin of the user to measure an ECG signal of the user. The amplifier may amplify the ECG signal measured by the first electrode through the third electrode. The digital converter may convert the amplified ECG signal into a digital signal, thereby extracting the ECG waveform.

The memory 420 may store, in advance, a registration data set including a plurality of registered waveforms extracted from a biosignal of a preregistered user.

The processor 430 may generate an authentication data set by extracting a plurality of waveforms for authenticating the user from the biosignal and perform one-to-one matching on each of the plurality of extracted authentication waveforms to the plurality of registered waveforms included in the registration data set, thereby calculating a similarity between each of the extracted authentication waveforms and the registered waveforms.

According to one example, the processor 430 may extract a feature for each of the plurality of extracted authentication waveforms and extract a feature for each of the plurality of registered waveforms, and calculate a similarity between the feature of each of the extracted authentication waveforms and the feature of each of the registered waveforms. Also, the processor 430 may extract a representative authentication waveform indicating a representative waveform of the extracted authentication waveforms and a representative registration waveform indicating a representative waveform of the registered waveforms, and calculate a similarity between the representative authentication waveform and the representative registration waveform.

The processor 430 may authenticate the user based on at least one of the similarity between the feature of each of the extracted authentication waveforms and feature of each of the registered waveforms and the similarity between the representative authentication waveform and the representative registration waveform.

The processor 430 may display information associated with a user authentication on the display 440. On the display 440, the processor 430 may display, for example, information on the biosignal of the user, information on an authentication waveform, information on a registered waveform, and/or information on a result of the user authentication.

Since the descriptions provided with reference to the data set generator 110, the similarity calculator 120, and the authenticator 130 of FIG. 1A, the data set generator 210, the similarity calculator 220, the auxiliary similarity calculator 230, and the authenticator 240 of FIG. 2, and the first feature extractor 310, the second feature extractor 320, the auxiliary feature extractor 330, the matcher 340, and the authenticator 350 of FIG. 3 are also applicable here, repeated descriptions with respect to the processor 430 of FIG. 4 will be omitted for increased clarity and conciseness.

Figure 5A:
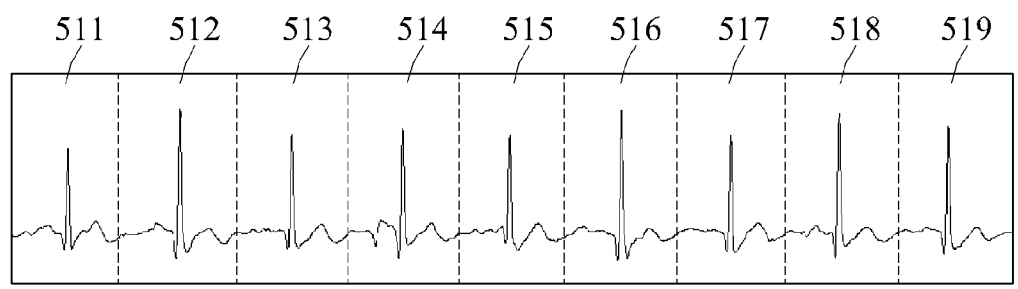
FIGS. 5A and 5B are diagrams illustrating an example of authenticating a user in an authentication apparatus.
Figure 5B:
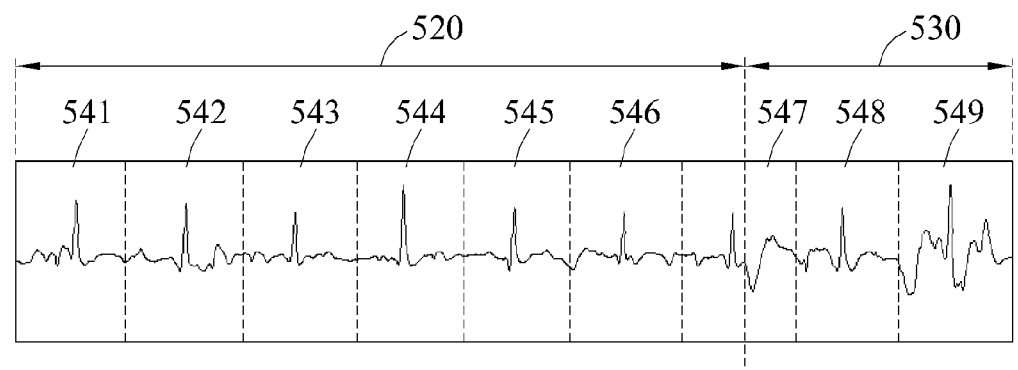

FIGS. 5A and 5B illustrate an example of a method of authenticating a user with an authentication apparatus.

FIGS. 5A and 5B illustrate graphs, each indicating an ECG waveform extracted from an ECG signal of a user attempting to be authenticated. In the graphs of FIGS. 5A and 5B, horizontal axes represent a time and vertical axes represent an amplitude of the ECG waveform.

The graph of FIG. 5A illustrates an ECG waveform of a user in a stable respiration state. The authentication apparatus may extract ECG waveforms 511 through 519 by dividing the ECG waveform of FIG. 5A based on a heart rate, and store each of the ECG waveforms 511 through 519 in an authentication data set stored in a memory. The authentication apparatus may perform one-to-one matching on each of the ECG waveforms 511 through 519 to a plurality of ECG waveforms included in a prestored registration data set in a memory and calculate a similarity between each of the ECG waveforms 511 through 519 to the ECG waveforms included in the prestored registration data set, thereby authenticating a user based on the calculated similarity.

The graph of FIG. 5B illustrates an ECG waveform of a user of which a respiration state is changed from stable to unstable. The user may stably breathe in a period of time 520 while breathing unstably in a period of time 530.

The authentication apparatus may extract ECG waveforms 541 through 549 by dividing the ECG waveform of FIG. 5B based on a heart rate. Since the user breathes in a stable state, a variation of the ECG waveforms 541 through 546 may be relatively small. In contrast, a variation of the ECG waveforms 547 through 549 may be relatively large due to an unstable respiration state of the user. The authentication apparatus may store each of the ECG waveforms 541 through 549 in the authentication data set. The authentication apparatus may authenticate the user based on the ECG waveforms 541 through 549. In the example, if the authentication apparatus extracts a representative ECG waveform from the ECG waveforms 541 through 549 and authenticates the user based on the representative ECG waveform only, then the representative ECG waveform may be distorted due to the ECG waveforms 547 through 549, which have a greater variation as compared to the ECG waveforms 541 through 546. Accordingly, the calculated FAR and FRR may incorrectly increase due to the variation.

In order to reduce the FAR and FRR, the authentication apparatus may perform one-to-one matching on each of the ECG waveforms 541 through 549 to the plurality of ECG waveforms included in the prestored registration data set and calculate a similarity between each of the ECG waveforms 541 through 549 to the ECG waveforms included in the prestored registration data set. The authenticating of the user may be based on the calculated similarity.

FIG. 6 illustrates an example of a method of calculating a similarity between an extracted authentication waveform and a registered waveform.

Referring to FIG. 6, an ECG waveform 610 indicates a registered waveform included in a registration data set and an ECG waveform 650 indicates an extracted authentication waveform included in an authentication data set. Hereinafter, the ECG waveform 610 may also be referred to as a registered waveform 610 and the ECG waveform 650 may also be referred to as an extracted authentication waveform 650.

An authentication apparatus may convert the registered waveform 610 into a frequency domain. As an example, the authentication apparatus may use an STFT to convert the registered waveform 610 into the frequency domain. Also, the authentication apparatus may generate a feature vector by reducing a dimension of a registered waveform 620 corresponding to the frequency domain into which the registered waveform 610 is converted. As an example, the authentication apparatus may reduce the dimension of the registered waveform 620 by selecting feature component 631 through 635 from the registered waveform 620 based on an LDA, and may acquire a feature vector 681 from a registered waveform 630 obtained by reducing the dimension of the registered waveform 620.

The authentication apparatus may convert the extracted authentication waveform 650 into a frequency domain. As an example, the authentication apparatus may use the STFT to convert the extracted authentication waveform 650 into the frequency domain. Also, the authentication apparatus may reduce a dimension of an extracted authentication waveform 660 corresponding to the frequency domain into which the extracted authentication waveform 650 is converted, by selecting feature component 671 through 675 from the extracted authentication waveform 660 based on the LDA, and may acquire a feature vector 682 from a registered waveform 670 obtained by reducing the dimension of the extracted authentication waveform 660.

The authentication apparatus may calculate a similarity between the feature vector 681 extracted based on the registered waveform 610 and the feature vector 682 extracted based on the extracted authentication waveform 650. For example, the authentication apparatus may calculate a similarity 683 between the feature vector 681 and the feature vector 682 based on a cosine similarity.

Figure 7:
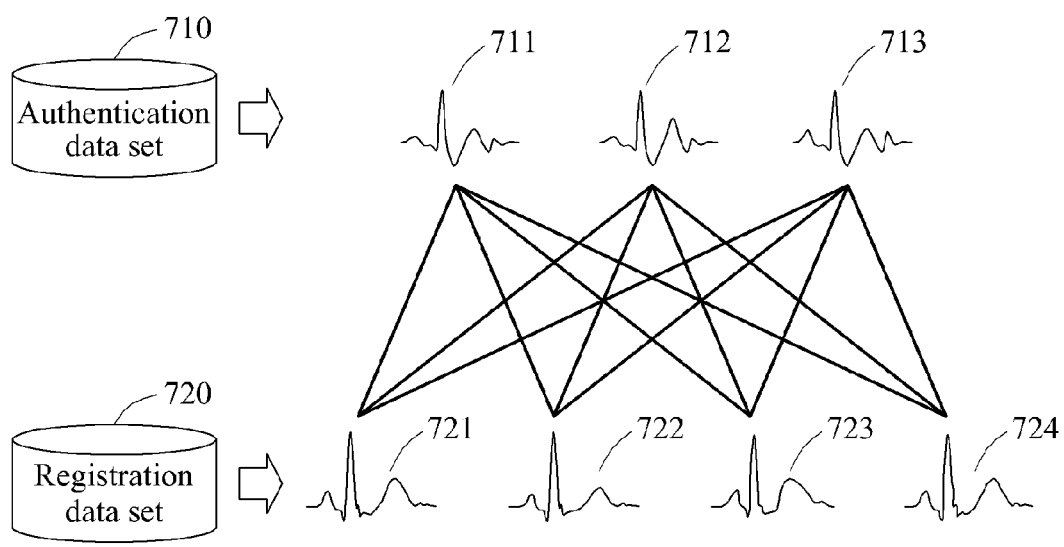
FIG. 7 is a block diagram illustrating an example of a method of matching an extracted waveform and a registered waveform.

FIG. 7 illustrates an example of a method of matching an extracted authentication waveform and a registered waveform.

Referring to FIG. 7, an authentication apparatus may perform one-to-one matching on each of three extracted authentication waveforms 711 through 713 included in an authentication data set 710 and each of four registered waveforms 721 through 724 included in a registration data set 720 and thus, the one-to-one matching may be performed 12 times. In FIG. 7, the extracted authentication waveforms 711 through 713 and the registered waveforms 721 through 724 may indicate a feature vector or a feature parameter. Through the one-to-one matching, the authentication apparatus may calculate a similarity between each of the extracted authentication waveforms 711 through 713 and each of the registered waveforms 721 through 724. For example, through the one-to-one matching of the extracted authentication waveform 711, the authentication apparatus may calculate a similarity between the extracted authentication waveform 711 and the registered waveform 721, a similarity between the extracted authentication waveform 711 and the registered waveform 722, a similarity between the extracted authentication waveform 711 and the registered waveform 723, and a similarity between the extracted authentication waveform 711 and the registered waveform 724.

In an example, the authentication apparatus may calculate the similarity between each of the extracted authentication waveforms 711 through 713 and each of the registered waveforms 721 through 724 based on, for example, a correlation, a cosine similarity, a Euclidean distance, an L1-norm, a P-norm, and an RMSE.

Figure 8:
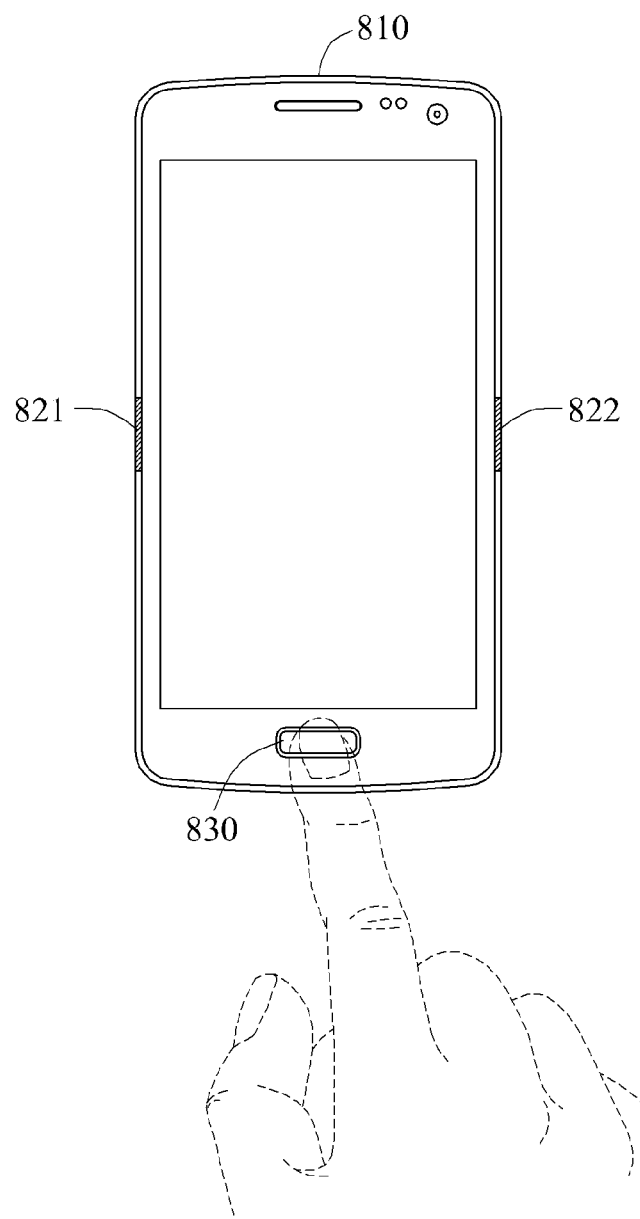
FIG. 8 is a diagram illustrating an example of an authentication apparatus.

FIG. 8 illustrates an example of an authentication apparatus.

Referring to FIG. 8, a mobile terminal 810 includes a positive pole electrode 821, a reference electrode 822, and a negative pole electrode 830 to sense an ECG signal. In an example, the positive pole electrode 821 and the reference electrode 822 may be disposed on both sides of the mobile terminal 810, and the negative pole electrode 830 may be disposed on a lower portion of the mobile terminal 810.

In this example, when a finger of a user contacts any one of the positive pole electrode 821, the reference electrode 822, and the negative pole electrode 830, the mobile terminal 810 may detect the ECG signal of the user. The mobile terminal 810 may amplify the ECG signal using an amplifier and convert the amplified ECG signal into a digital signal using a digital filter. The mobile terminal 810 may extract an ECG waveform from the digital signal obtained by converting the ECG signal [LC5].

During registration, the ECG waveform of a user is registered. The mobile terminal 810 may acquire an ECG signal of the user using the plurality of electrodes and divide the acquired ECG signal based on a heart rate, thereby extracting a plurality of waveforms for registration. The mobile terminal 810 may incorporate the extracted waveforms into a registration data set. The mobile terminal may store the registration data set in a memory.

When a user is being authenticated, the mobile terminal 810 may acquire an ECG signal of the user using the plurality of electrodes and divide the acquired ECG signal based on a heart rate, thereby extracting a plurality of extracted authentication waveforms. The mobile terminal 810 may incorporate the extracted authentication waveforms in an authentication data set. The mobile terminal 810 may perform one-to-one matching on each of the extracted authentication waveforms included in the authentication data set to the registered waveforms included in the registration data set, thereby calculating a similarity between each of the extracted authentication waveforms and the registered waveforms. Also, the mobile terminal 810 may extract a representative authentication waveform from the extracted authentication waveforms and extract a representative registration waveform from the registered waveforms, thereby calculating a similarity between the representative authentication waveform and the representative registration waveform. The mobile terminal 810 may authenticate whether the user attempting to be authenticated matches a preregistered user based on the similarity between each of the extracted authentication waveforms and the registered waveforms and the similarity between the representative authentication waveform and the representative registration waveform.

Figure 9:
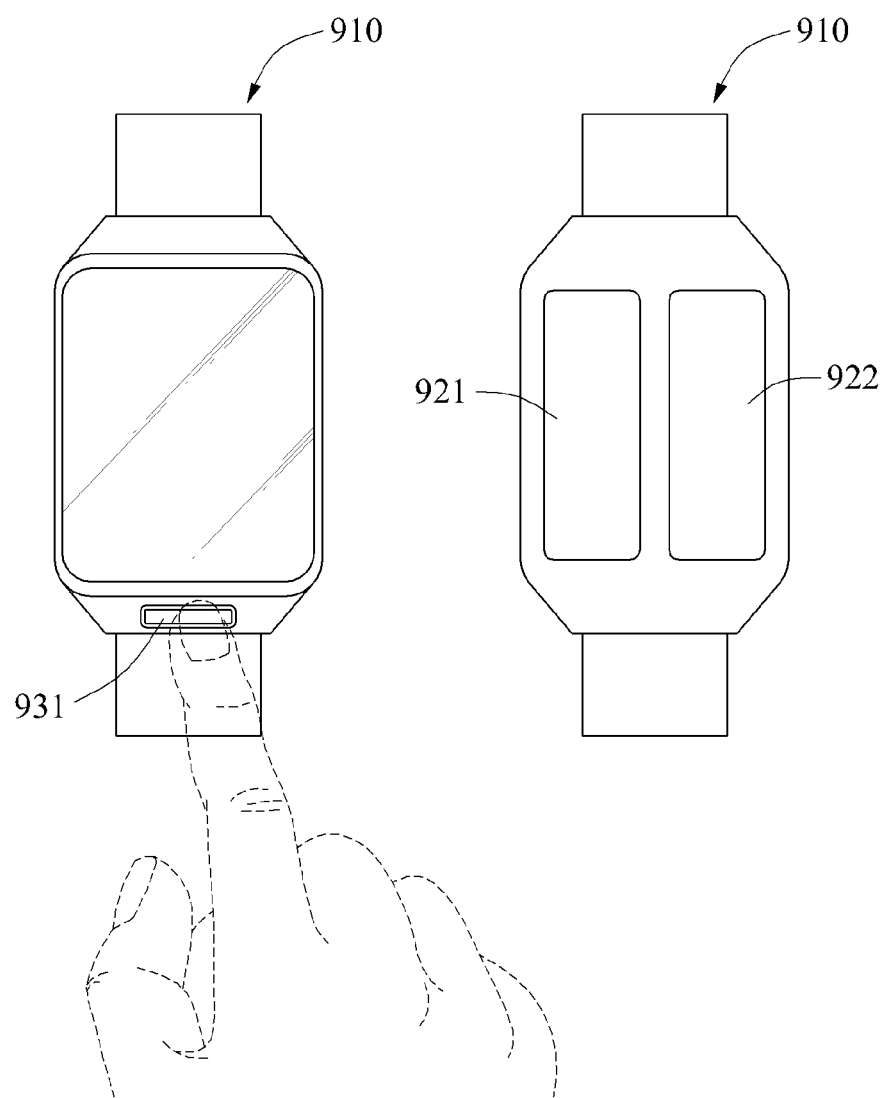
FIG. 9 is a diagram illustrating another example of an authentication apparatus.

FIG. 9 illustrates another example of an authentication apparatus.

Referring to FIG. 9, a wearable terminal 910 includes a positive pole electrode 921, a reference electrode 922, and a negative pole electrode 931 to sense an ECG signal. In an example, the positive pole electrode 921 and the reference electrode 922 may be disposed on a rear side of the wearable terminal 910, and the negative pole electrode 931 may be disposed on a front side of the wearable terminal 910.

Similar to the mobile terminal 810 of FIG. 8, the wearable terminal 910 may acquire an ECG signal of a user using a plurality of electrodes, for example, the positive pole electrode 921, the reference electrode 922, and the negative pole electrode 931 and extract an ECG waveform from the ECG signal, thereby filtering the extracted ECG waveform. Also, the wearable terminal 910 may perform an identical operation to the operation of the mobile terminal 810 of the FIG. 8 to register an ECG waveform of a user in advance, or authenticate whether a user attempting to be authenticated matches a preregistered user.

Figure 10:
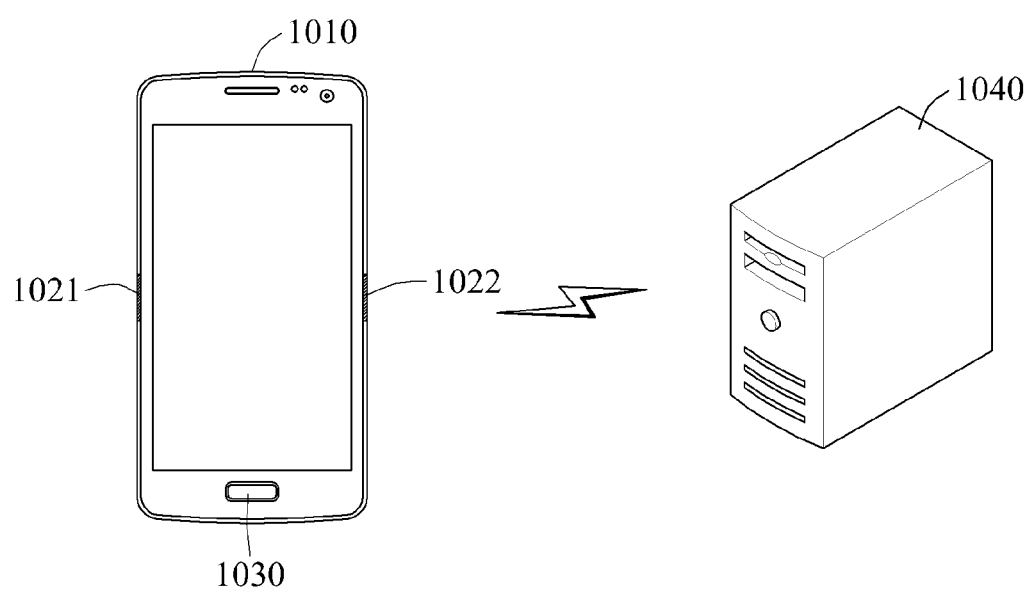
FIG. 10 is a diagram illustrating still another example of an authentication apparatus.

FIG. 10 illustrates another example of an authentication apparatus. In this example, the authentication apparatus is a mobile terminal.

Referring to FIG. 10, the mobile terminal 1010 includes a positive pole electrode 1021, a reference electrode 1022, and a negative pole electrode 1030 to sense an ECG signal. In an example, the positive pole electrode 1021 and the reference electrode 1022 may be disposed on both sides of the mobile terminal 1010, and the negative pole electrode 1030 may be disposed on a lower portion of the mobile terminal 1010.

The mobile terminal 1010 may acquire an ECG signal of a user using a plurality of electrodes, for example, the positive pole electrode 1021, the reference electrode 1022, and the negative pole electrode 1030 and divide the acquired ECG signal based on a heart rate, thereby extracting a plurality of extracted authentication waveforms. The mobile terminal 1010 may incorporate the extracted authentication waveforms in an authentication data set.

In an example, the mobile terminal 1010 may receive information associated with a registration data set from a server 1040 through a communication interface. The communication interface may include, for example, a wireless Internet interface such as a wireless local area network (WLAN), a wireless fidelity (WiFi) direct, a digital living network alliance (DLNA), a wireless broadband (WiBro), a world interoperability for microwave access (WiMAX), a high speed downlink packet access (HSDPA), and the like, and a local area communication interface such as a Bluetooth™, a radio frequency identification (RFID), an infrared data association (IrDA), an ultra wideband (UWB), ZigBee, a near field communication (NFC), and the like. Also, the communication interface may indicate any interface, for example, a wired interface, used to communicate with the server 1040.

The mobile terminal 1010 may perform one-to-one matching on each of the extracted authentication waveforms included in the authentication data set to a plurality of registered waveforms included in the registration data set, thereby calculating a similarity between each of the extracted authentication waveforms and the registered waveforms. Also, the mobile terminal 1010 may extract a representative authentication waveform from the extracted authentication waveforms and extract a representative registration waveform from the registered waveforms, thereby calculating a similarity between the representative authentication waveform and the representative registration waveform. The mobile terminal 1010 may authenticate whether a user attempting to be authenticated matches a preregistered user based on the similarity between each of the extracted authentication waveforms and the registered waveforms and the similarity between the representative authentication waveform and the representative registration waveform.

The mobile terminal 1010 may transmit, for example, information on the ECG signal of the user, information on an extracted authentication waveform, and information on a user authentication result, to the server 1040. In an example, the server 1040 may allow the user to access the server 1040 based on the information on the user authentication received from the mobile terminal 1010.

Figure 11:
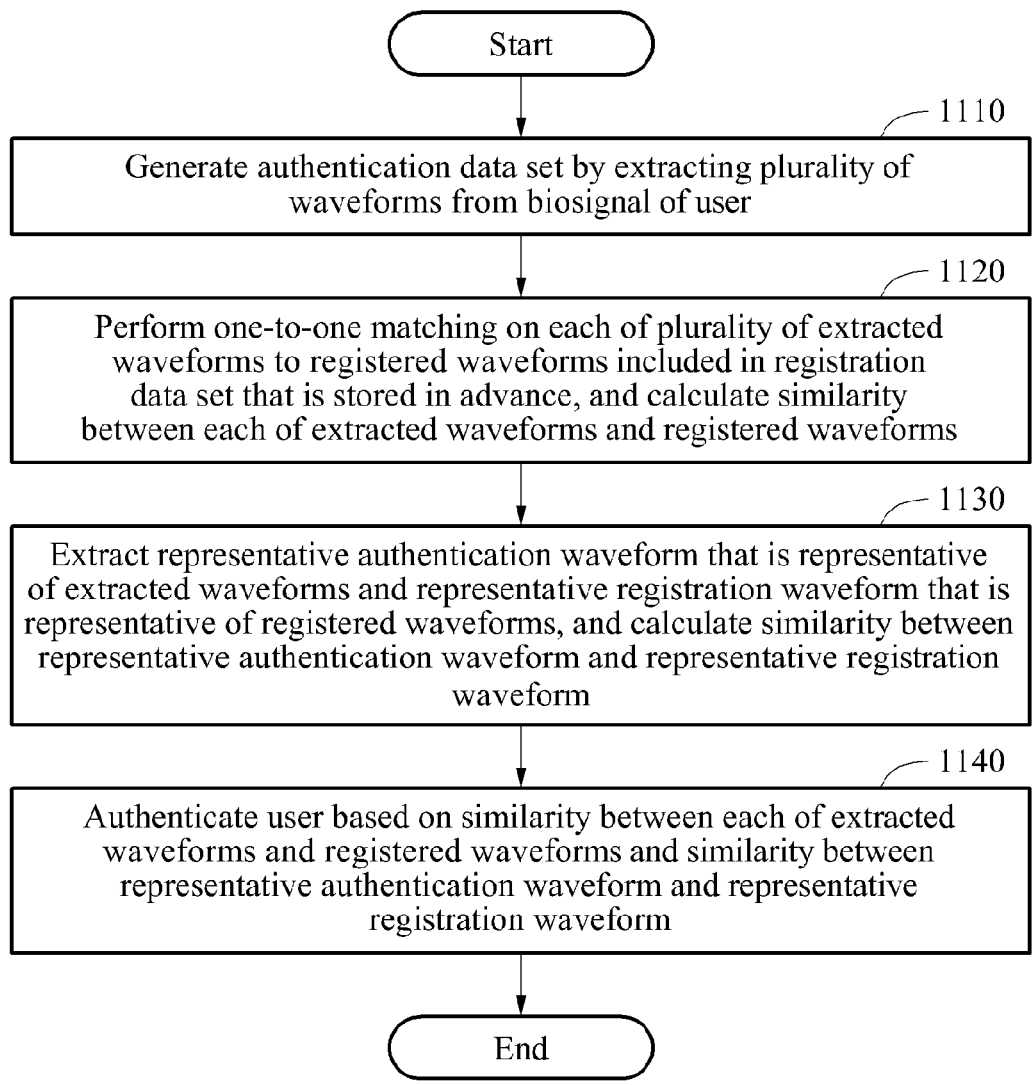
FIG. 11 is a flowchart illustrating an example of an authentication method.

FIG. 11 illustrates an example of an authentication method.

Referring to FIG. 11, in operation 1110, an authentication apparatus generates an authentication data set by extracting a plurality of waveforms for authenticating a user from a biosignal of the user.

In operation 1120, the authentication apparatus performs one-to-one matching on each of the plurality of extracted authentication waveforms to a plurality of registered waveforms included in a registration data set that is stored in advance, and calculates a similarity between each of the extracted authentication waveforms and the registered waveforms.

In operation 1130, the authentication apparatus extracts a representative authentication waveform indicating a representative waveform of the extracted authentication waveforms and a representative registration waveform indicating a representative waveform of the registered waveforms, and calculates a similarity between the representative authentication waveform and the representative registration waveform.

In operation 1140, the authentication apparatus authenticates the user based on the similarity between each of the extracted authentication waveforms and the registered waveforms and the similarity between the representative authentication waveform and the representative registration waveform.

Since the descriptions provided with reference to FIGS. 1A through 10 are also applicable here, repeated descriptions with respect to the authentication method of FIG. 11 will be omitted for increased clarity and conciseness.

The various modules, elements, and methods described above may be implemented using one or more hardware components, one or more software components, or a combination of one or more hardware components and one or more software components.

A hardware component may be, for example, a physical device that physically performs one or more operations, but is not limited thereto. Examples of hardware components include resistors, capacitors, inductors, power supplies, frequency generators, operational amplifiers, power amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Functional programs, codes, and code segments for implementing the examples disclosed herein can be easily constructed by a programmer skilled in the art to which the examples pertain based on the drawings and their corresponding descriptions as provided herein.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

The apparatuses, units, modules, devices, generator, calculator, authenticator, matcher, extractor and other components illustrated in FIGS. 1A, 2, 3 and 4 that perform the operations described herein with respect to FIGS. 6, 7 and 11 are implemented by hardware components. Examples of hardware components include controllers, sensors, generators, drivers, display, memory and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 6, 7 and 11. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 6, 7 and 11 are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An authentication apparatus comprising:
   a sensor configured to detect a biosignal of a user; and
   a processor configured to
      extract a plurality of waveforms from the detected biosignal,
      obtain a plurality of registered waveforms of a stored biosignal of a registered user,
      match each waveform of the plurality of waveforms to each registered waveform of the plurality of registered waveforms, such that each waveform is matched to every registered waveform
      calculate a similarity for each matched waveform and each matched registered waveform,
      extract a representative authentication waveform indicating a representative waveform of the extracted waveforms and a representative registration waveform indicating a representative waveform of the registered waveforms,
      calculate a representative similarity between the representative authentication waveform and the representative registration waveform, and
      authenticate the user based on each similarity between each waveform and each registered waveform and the representative similarity.

2. The apparatus of claim 1, wherein the biosignal comprises an electrocardiogram (ECG) signal.

3. The apparatus of claim 1, further comprising a memory configured to store the registered waveforms of the stored biosignal of the registered user during a registration performed prior to authentication of the user.

4. The apparatus of claim 1, wherein the processor is further configured to extract a feature of each of the extracted waveforms and a feature of each of the registered waveforms, and to calculate a similarity between the feature of each of the extracted waveforms and the feature of every registered waveform.

5. The apparatus of claim 4, wherein the processor is further configured to convert each of the extracted waveforms into a corresponding feature vector and each of the registered waveforms into a corresponding registered feature vector, and to calculate a similarity between each feature vector and every registered feature vector.

6. The apparatus of claim 5, wherein the processor is further configured to change dimensions of each of the extracted waveforms and each of the registered waveforms, and to convert each of the extracted waveforms into the corresponding feature vector and each of the registered waveforms into the corresponding registered feature vector.

7. The apparatus of claim 4, wherein the processor is further configured to extract a feature parameter of each extracted waveform and a feature parameter of each registered waveform, and to calculate a similarity between the feature parameter of each extracted waveform and the feature parameter of every registered waveform.

8. The apparatus of claim 7, wherein the feature parameters comprise at least one of a PR interval, a PR segment, a QRS complex, an ST segment, an ST interval, a QT interval, an RR interval, an amplitude, or noise power of each registered waveform or each extracted waveform.

9. The apparatus of claim 1, wherein the processor is further configured to extract a feature of the representative extracted waveform and a feature of the representative registration waveform, and to calculate the representative similarity between the feature of the representative authentication waveform and the feature of the representative registration waveform.

10. The apparatus of claim 9, wherein the processor is further configured to convert the representative authentication waveform into a representative authentication feature vector, to convert the representative registration waveform into a representative registration feature vector, and to calculate the representative similarity between the representative authentication feature vector and the representative registration feature vector.

11. The apparatus of claim 9, wherein the processor is further configured to extract a feature parameter of the representative authentication waveform and a feature parameter of the representative registration waveform, and to calculate a similarity between the feature parameter of the representative authentication waveform and the feature parameter of the representative registration waveform.

12. The apparatus of claim 9, wherein the processor is further configured to determine whether the user matches the registered user based on the representative similarity and each similarity between each extracted waveform and every registered waveform.

13. The apparatus of claim 12, wherein the processor is further configured to normalize the representative similarity and each similarity between each extracted waveform and every registered waveform.

14. The apparatus of claim 12, wherein the processor is further configured to set a different respective weight to the representative similarity and to each similarity between each extracted waveform and every registered waveform.

15. The apparatus of claim 14, wherein the processor is further configured to set the different respective weights by:
calculating an average similarity based on the representative similarity and on each calculated similarity between each waveform and every registered waveform;
assigning a greater weight to the representative similarity or a similarity between a waveform and a registered waveform if the representative similarity or the similarity between the waveform and the registered waveform is greater than the average similarity; and
assigning a lesser weight to the representative similarity or the similarity between the waveform and the registered waveform if the representative similarity or the similarity between the waveform and the registered waveform is less than the average similarity.

16. The apparatus of claim 12, wherein the processor is further configured to determine whether the extracted waveforms match the registered waveforms by applying, to a classifier, the representative similarity and each similarity between each extracted waveform and registered waveform.

17. The apparatus of claim 16, wherein the classifier comprises at least one of a support vector machine (SVM) and a nearest neighbor (NN).

18. The apparatus of claim 1, wherein the processor is further configured to, in response to a failure to authenticate the user, iterate the operations of detecting a biosignal of the user, extracting a plurality of waveforms from the detected biosignal, obtaining the plurality of registered waveforms of the stored biosignal of the registered user, matching each waveform of the plurality of waveforms to each registered waveform of the plurality of registered waveforms, calculating a similarity for each matched waveform and each matched registered waveform, extracting a representative authentication waveform indicating a representative waveform of the extracted waveforms and a representative registration waveform indicating a representative waveform of the registered waveforms, calculating a representative similarity between the representative authentication waveform and the representative registration waveform, and authenticating the user based on each similarity between each waveform and each registered waveform and the representative similarity.

19. The apparatus of claim 18, wherein the processor is further configured to, in response to iterating the operations a threshold number of times, determine that the user differs from the registered user.

20. The apparatus of claim 1, wherein:
a number of extracted waveforms is M, wherein M is greater than or equal to 2;
a number of registered waveforms is N, wherein N is greater than or equal to 2; and
the processor is configured to match each waveform of the plurality of waveforms to each registered waveform of the plurality of registered waveforms, such that matching is performed M*N times.

21. An authentication method comprising:
detecting a biosignal of a user;
extracting a plurality of waveforms from the detected biosignal of the user;
obtaining a plurality of registered waveforms of a stored biosignal of a registered user;
matching each extracted waveform of the plurality of waveforms to each registered waveform of the plurality of registered waveforms such that each extracted waveform is matched to every registered waveform;
calculating a similarity for each matched waveform and each matched registered waveform; and
authenticating the user based on each similarity between each extracted waveform and each registered waveform.

22. The method of claim 21, wherein the extracting of the plurality of waveforms from the detected biosignal of the user comprises:
determining a quality of each extracted waveform of the plurality of waveforms; and
excluding an extracted waveform having a quality lower than a threshold quality value.

23. The method of claim 21, further comprising:
extracting a representative authentication waveform indicating a representative waveform of the extracted waveforms and a representative registration waveform indicating a representative waveform of the registered waveforms; and
calculating a representative similarity between the representative authentication waveform and the representative registration waveform.

24. A non-transitory computer-readable storage medium storing therein a program comprising instructions to cause a computer to:
detect a biosignal of a user;
extract a plurality of waveforms from the detected biosignal of the user;

obtain a plurality of registered waveforms of a stored biosignal of a registered user;
match each extracted waveform of the plurality of waveforms to each registered waveform of the plurality of registered waveforms such that each extracted waveform is matched to every registered waveform;
calculate a similarity for each matched waveform and each matched registered waveform; and
authenticate the user based on each similarity between each extracted waveform and each registered waveform and the representative similarity.

\* \* \* \* \*